United States Patent
Inoue et al.

(10) Patent No.: US 6,866,636 B2
(45) Date of Patent: Mar. 15, 2005

(54) CUFF FOR BLOOD PRESSURE MONITOR (75) Inventors: Tomonori Inoue, Kyoto (JP);
Yoshihiko Sano, Kyoto (JP); Takahide Tanaka, Kyoto (JP); Takashi Inagaki, Kyoto (JP); Minoru Taniguchi, Kyoto (JP)

(73) Assignee: Omron Corporation, Kyoto (JP)

( * ) Notice: Subject to any disclaimer, the term of this patent is extended or adjusted under 35 U.S.C. 154(b) by 79 days.

(21) Appl. No.: 10/461,868

(22) Filed: Jun. 16, 2003

(65) Prior Publication Data
US 2004/0034308 A1 Feb. 19, 2004

(30) Foreign Application Priority Data
Jun. 18, 2002 (JP) ........................................ 2002-177273

(51) Int. Cl.[7] ............................. A61B 5/02; A61B 17/00
(52) U.S. Cl. .................... 600/499; 600/490; 606/202
(58) Field of Search .................... 600/499, 493–497, 600/490, 481, 485, 500–503; 602/13, 27, 20–23; 606/202–203

(56) References Cited

U.S. PATENT DOCUMENTS 6,245,023 B1 * 6/2001 Clemmons .................. 600/499
6,346,083 B1 * 2/2002 Nishibayashi et al. ...... 600/490
6,527,727 B2 * 3/2003 Itonaga et al. .............. 600/499
6,785,821 B1 * 8/2004 Teal ............................ 713/200

FOREIGN PATENT DOCUMENTS

| JP | 01072726 A | * | 3/1989 | ............. A61B/5/02 |
| JP | 02107226 A | * | 4/1990 | ............. A61B/5/22 |
| JP | 05049529 A | * | 3/1993 | ............. A47C/27/08 |
| JP | 09117419 A | * | 5/1997 | ............. A61B/5/022 |
| JP | 2840075 | * | 10/1998 | ............. A61B/5/022 |
| JP | 11342118 A | * | 12/1999 | ............. A61B/5/022 |
| JP | 2001-224558 | | 8/2001 | |

* cited by examiner

Primary Examiner—Eric F. Winakur
Assistant Examiner—Navin Natnithithadha
(74) Attorney, Agent, or Firm—Morrison & Foerster LLP (57) ABSTRACT

In a cuff of a blood pressure monitor, a distance along bending of a first expandable portion is set so as to be different from a distance along bending of a second expandable portion at the time of deflation. When a fluid bladder for pressurizing is inflated with a fluid fed thereinto, the second expandable portion expands longer. As a result, force, which is generated on a cuff fixing element which is pushed by the fluid bladder for pressurizing, acts to a vertical direction with respect to an axial direction of a subject.

5 Claims, 8 Drawing Sheets

BEFORE PRESSURIZING

Prior Art

Fig. 12

AFTER PRESSURIZING

Prior Art

CUFF FOR BLOOD PRESSURE MONITOR

BACKGROUND OF THE INVENTION

1. Field of the Invention

The present invention relates to a blood pressure monitor which is mounted on a subject to measure blood pressure and, more particularly, to a structure of a cuff of a blood pressure monitor which is wound around a brachium or a wrist and pressurizes the portion to be measured, thereby measuring blood pressure.

2. Description of the Related Art

A structure of a cuff of a blood pressure monitor to be used for a blood pressure monitor which is mounted on a subject so as to measure blood pressure is disclosed in, for example, JP P2001-224558A. The structure of the cuff of a blood pressure monitor, particularly a structure of a fluid bladder for pressurizing mounted on the cuff of a blood pressure monitor will be described with reference to FIGS. 11 and 12.

Figure 11:
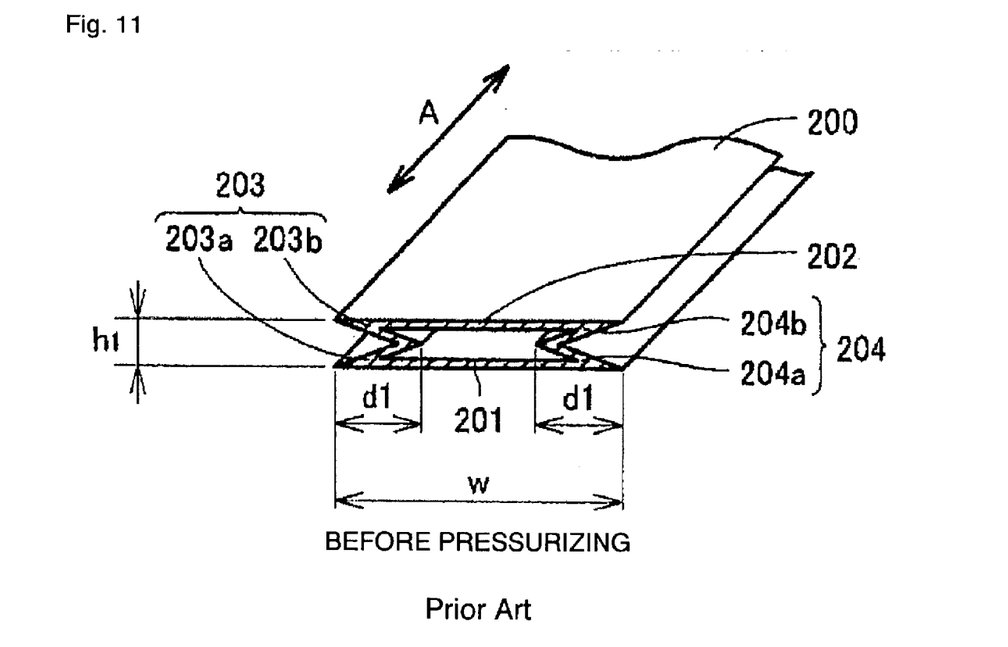
FIG. 11 is a first perspective view showing the entire structure of a conventional fluid bladder 200 for pressurizing.

With reference to FIG. 11, a conventional fluid bladder 200 for pressurizing has an inside belt 201, an outside belt 202, a first expandable portion 203 and a second expandable portion 204. The inside belt 201 is positioned on a side of a subject. The outside belt 202 is provided on a position opposed to the inside belt 201. The first expandable portion 203 and the second expandable portion 204 are provided so as to connect the inside belt 201 and the outside belt 202 on both side portions with respect to a direction in which the cuff of a blood pressure monitor is wound around a brachium, a wrist and the other subject (direction A in FIG. 11). When the fluid bladder 200 for pressurizing is deflated, as shown in FIG. 11, the first expandable portion 203 and the second expandable portion 204 are bent inward.

The first expandable portion 203 has a side portion 203a at the inside belt side whose one end is connected with the inside belt 201, and a side portion 203b at the outside belt side whose one end is connected with the outside belt 202. The other ends of the side portion 203a at the inside belt side and the side portion 203b at the outside belt side are connected, so that an approximately Σ shaped form is configured. The second expandable portion 204 has a side portion 204a at the inside belt side and a side portion 204b at the outside belt side similarly to the first expandable portion 203.

Figure 12:
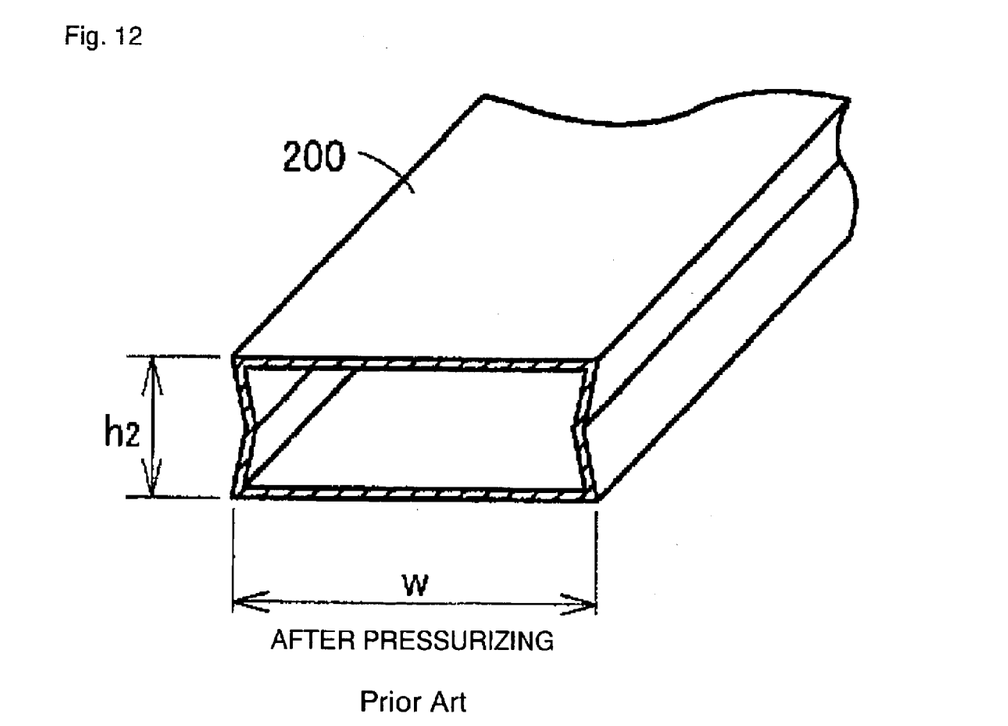
FIG. 12 is a second perspective view showing the entire structure of the conventional fluid bladder 200 for pressurizing.

Widths of the inside belt 201 and the outside belt 202 are set to a predetermined dimension W. Also after the fluid bladder 200 for pressurizing is inflated as shown in FIG. 12, the width dimension W is approximately maintained. A distance d1 along the bending of the first expandable portion 203 and the second expandable portion 204 at the time of deflation are set to the approximately same dimension, and the first expandable portion 203 and the second expandable portion 204 have the same expandability. After the fluid bladder 200 for pressurizing is inflated, the first expandable portion 203 and the second expandable portion 24 expand by the same length (h1 in FIG. 11→h2 in FIG. 12), so that the fluid bladder for pressurizing 200 can be inflated.

SUMMARY OF THE INVENTION

It is an object of the present invention to provide a cuff of a blood pressure monitor capable of efficiently applying pressure to a subject (artery).

According to the present invention, in a cuff of a blood pressure monitor configured to be mounted on a predetermined portion of a subject and including a bladder configured to expand to pressurize the predetermined portion of the subject upon inflation with a fluid, the bladder includes an inside belt configured to be placed over the predetermined portion of the subject when the cuff is mounted on the predetermined portion of the subject, an outside belt disposed over the inside belt, a first expandable portion connecting a longitudinal side of the inside belt and a corresponding side of the outside belt, and a second expandable portion connecting another longitudinal side of the inside belt and a corresponding side of the outside belt. The second expandable portion is configured to expand more than the first expandable portion when the bladder is inflated with the fluid for pressurizing the predetermined portion of the subject.

DETAILED DESCRIPTION OF THE INVENTION

Hereinafter, embodiments of a cuff of a blood pressure monitor according to the present invention will be described with reference to the drawings. The structure of the fluid bladder for pressurizing, which is fixed to a subject by a cuff fixing element in the cuff of a blood pressure monitor, will be described in detail herein. Structures of the cuff fixing element and the blood pressure monitor are similar to those disclosed in, for example, JP P2001-224558A.

Figure 13:
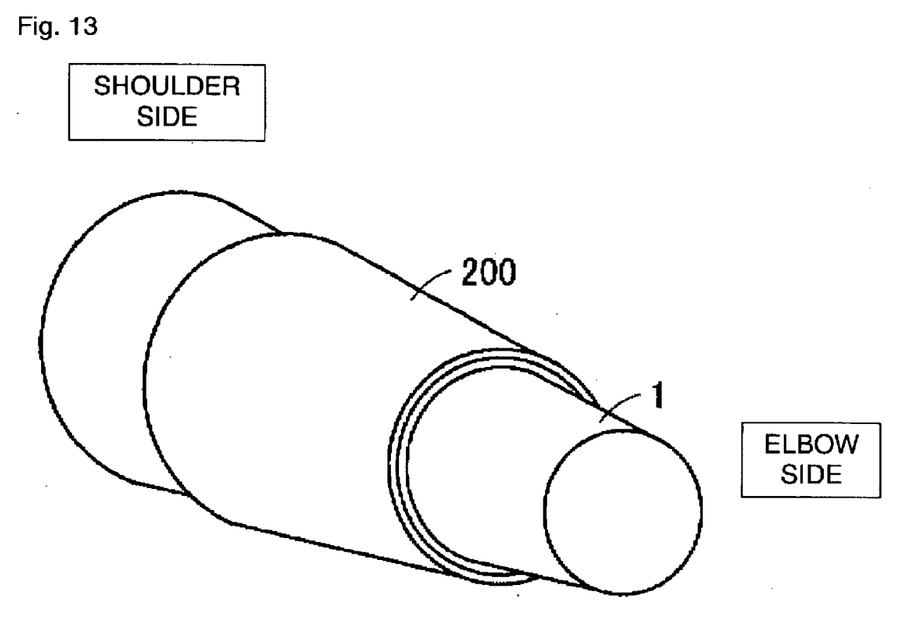
FIG. 13 is a perspective view showing a state where the fluid bladder 200 for pressurizing is wound around the brachium 1 by the cuff fixing element 201.
Figure 14:
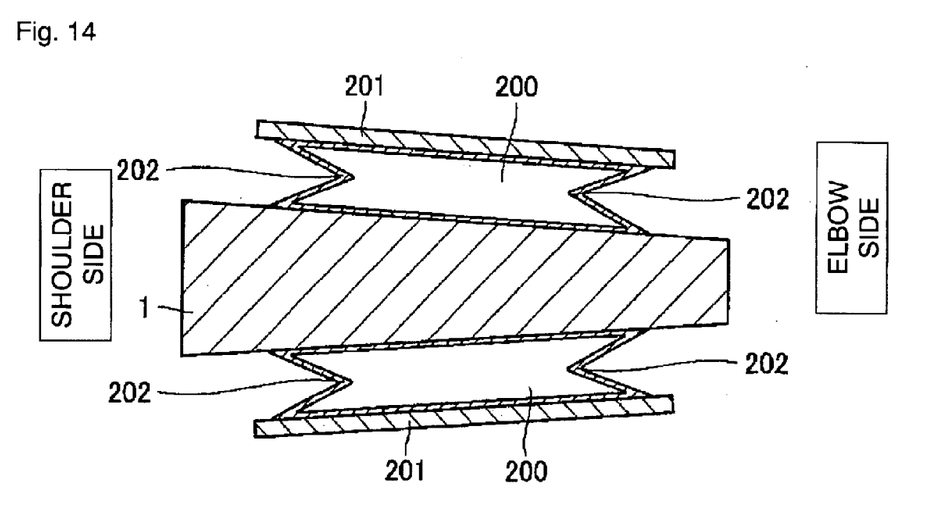
FIG. 14 is a schematic diagram showing a state where the fluid bladder 200 for pressurizing is wound around the brachium 1 by the cuff fixing element 201 and the fluid bladder for pressurizing 200 is not inflated.
Figure 15:
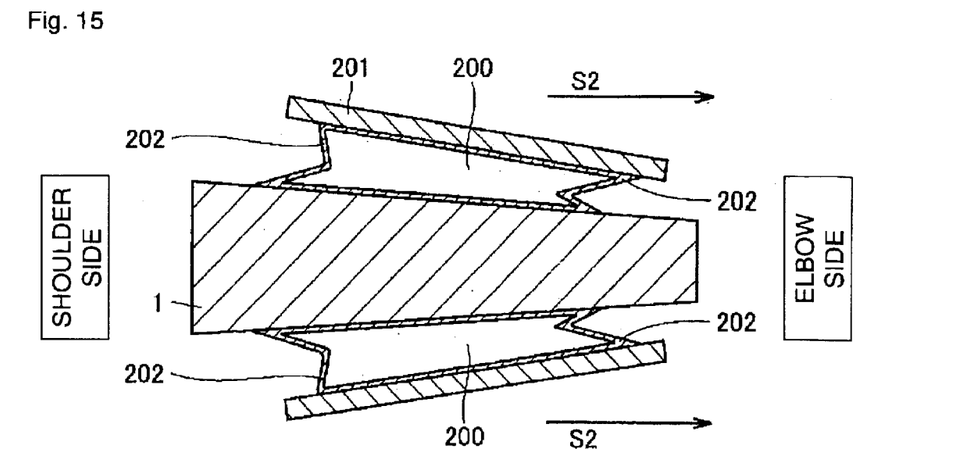
FIG. 15 is a schematic diagram showing a state where the fluid bladder 200 for pressurizing is wound around the brachium 1 by the cuff fixing element 201 and the fluid bladder 200 for pressurizing is inflated.

As shown in FIGS. 13 and 14, in the case where a conventional fluid bladder 200 for pressurizing is wound around, for example, a brachium 1 by a cuff fixing element 201, the brachium 1 has different thickness on an elbow side and a shoulder side. More specifically, when a fluid is supplied to the fluid bladder 200 for pressurizing so that it is inflated, as shown in FIG. 15, a phenomenon that the cuff fixing element 201 and the fluid bladder 200 for pressurizing shift to the elbow side (to direction S2 in FIG. 15) occurs due to a so-called tapered surface shape of the brachium 1. This phenomenon will be described in detail with reference to FIGS. 16 to 19.

Figure 16:
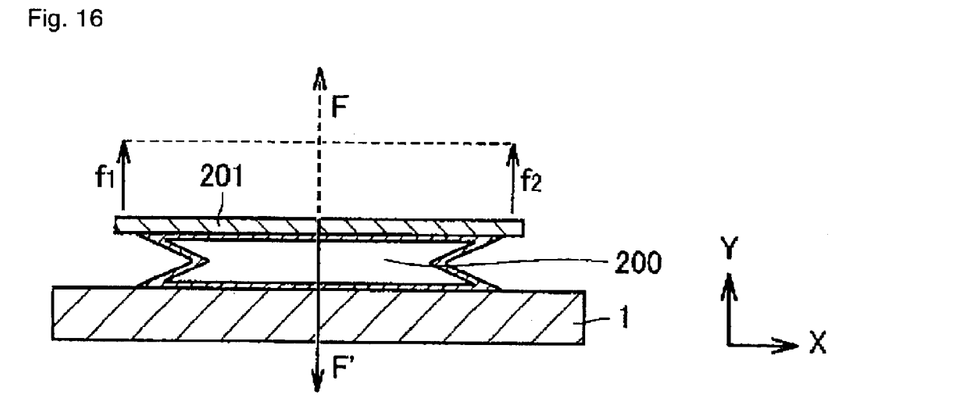
FIG. 16 is a first schematic diagram for describing a operational principle of the inflation of the fluid bladder 200 for pressurizing.

With reference to FIG. 16, in the case where the fluid bladder 200 for pressurizing is wound around a subject 1 in a horizontal state by the cuff fixing element 201, when the fluid bladder 200 for pressurizing is inflated, the cuff fixing element 201 is pushed by the fluid bladder 200 for pressurizing and receives a force F. As its counteraction, the cuff fixing element 201 pushes back the fluid bladder 200 for pressurizing by means of a force F' which has the same strength as the force F. The force F is a sum of forces received by respective parts of the cuff fixing element 201. When the forces of the respective parts are represented by forces f1, f2 which act on both ends of the cuff fixing element 201, taking symmetry of the cuff fixing element 201 and the fluid bladder 200 for pressurizing into consideration, a relationship, f1=f2, is established. A direction of F is vertical to an axial direction of the subject (X axial direction in FIG. 16), that is, it is considered as a direction separated from the subject 1 (Y axial direction in FIG. 16).

With this structure, the cuff fixing element 201 pushes the fluid bladder 200 for pressurizing vertically with respect to the axial direction of the subject 1 (X axial direction), so that balance between the fluid bladder 200 for pressurizing and the cuff fixing element 201 is not lost and the fluid bladder 200 for pressurizing pressurizes the subject 1 properly.

Figure 17:
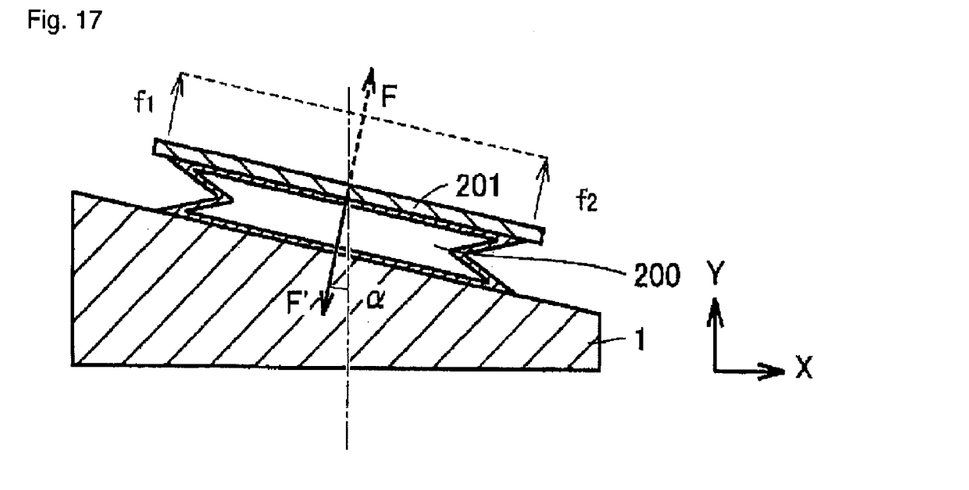
FIG. 17 is a second schematic diagram for describing the operational principle of the inflation of the fluid bladder 200 for pressurizing.
Figure 18:
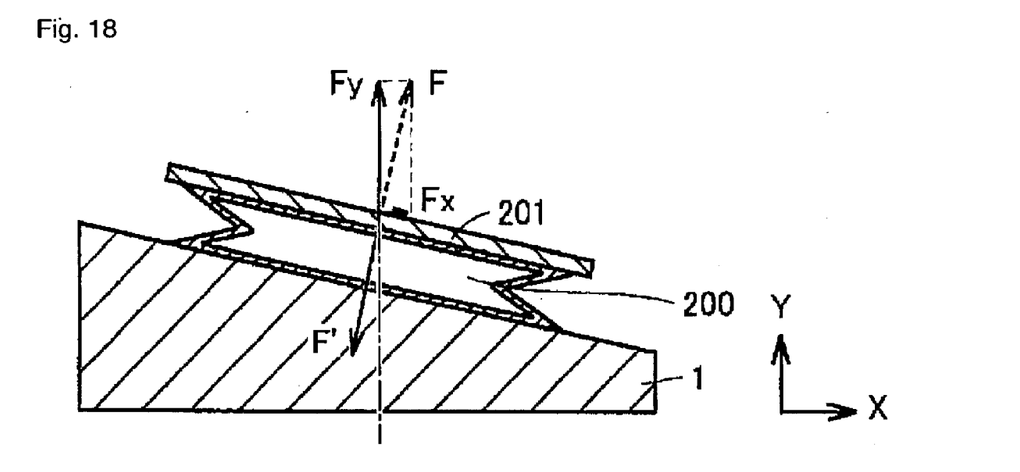
FIG. 18 is a third schematic diagram for describing the operational principle of the inflation of the fluid bladder 200 for pressurizing.
Figure 19:
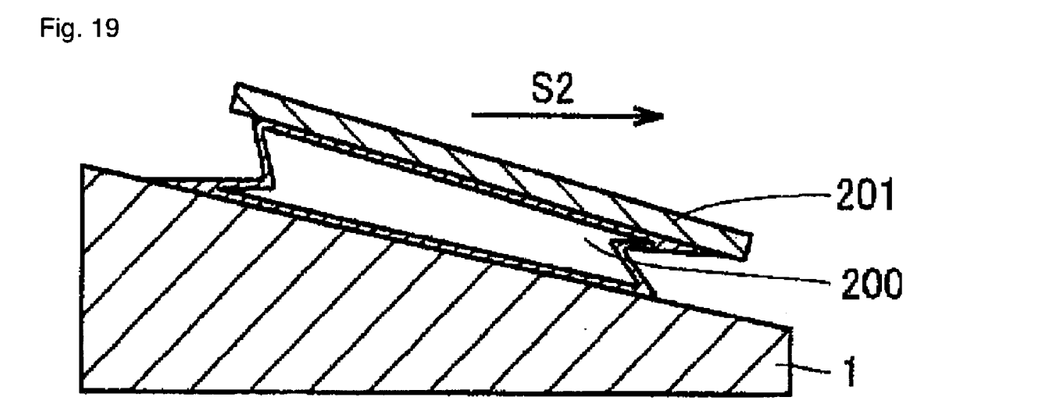
FIG. 19 is a fourth schematic diagram for describing the operational principle of the inflation of the fluid bladder 200 for pressurizing.

With reference to FIGS. 17 to 19, the case where the fluid bladder 200 for pressurizing is wound around the subject 1 having a tapered surface by the cuff fixing element 201 will be described. With reference to FIG. 17, when the fluid bladder 200 for pressurizing is inflated, similarly to the above case, the cuff fixing element 201 is pushed by the fluid bladder 200 for pressurizing and receives the force F. As the counteraction, the cuff fixing element 201 pushes back the fluid bladder 200 for pressurizing by means of the force F' which is the same strength as the force F.

In the case where the subject 1 has the tapered surface, however, the force F vertical to the subject 1 tilts by α with respect to the Y axial direction. At this time, as shown in FIG. 18, a force FX which shifts to the X axial direction is generated in the balance of the forces acting on the cuff fixing element 201. When the force FX is generated, as shown in FIG. 19, the cuff fixing element 201 is shifted (direction S2 in the figure: the elbow side in the case of the brachium).

When the cuff fixing element 201 and the fluid bladder 200 for pressurizing shift in such a manner, a center of pressurizing by means of the fluid bladder 200 for pressurizing shifts. For this reason, it was confirmed that proper pressure cannot be applied to an artery effectively. As a result, the conventional fluid bladder 200 for pressurizing should be inflated excessively in order to compensate insufficient pressurizing force, and thus excessive tension is generated in the fluid bladder 200 for pressurizing. For this reason, measurement of blood pressure is disturbed, and a fluid pump cannot be miniaturized. The blood pressure monitor cannot be therefore miniaturized.

Figure 1:
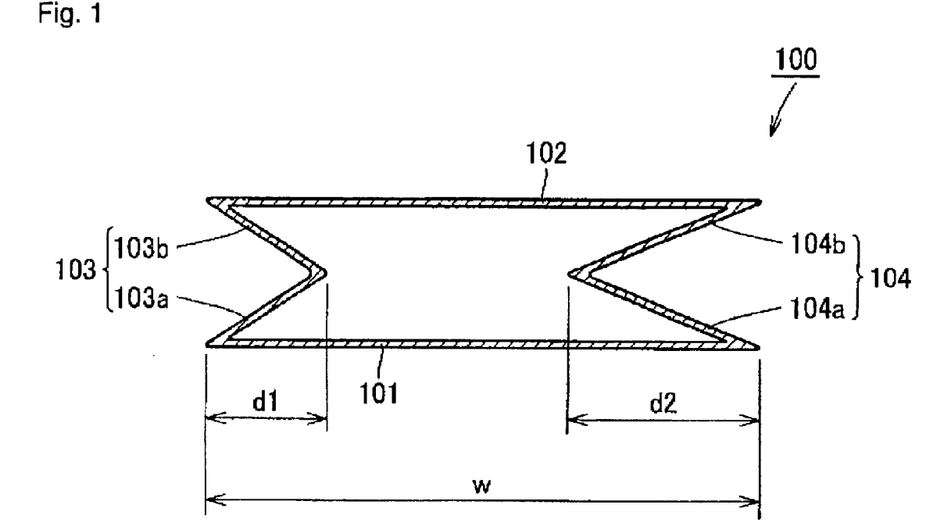
FIG. 1 is a cross sectional view showing a structure of a fluid bladder 100 for pressurizing according to an embodiment of the present invention.
Figure 2:
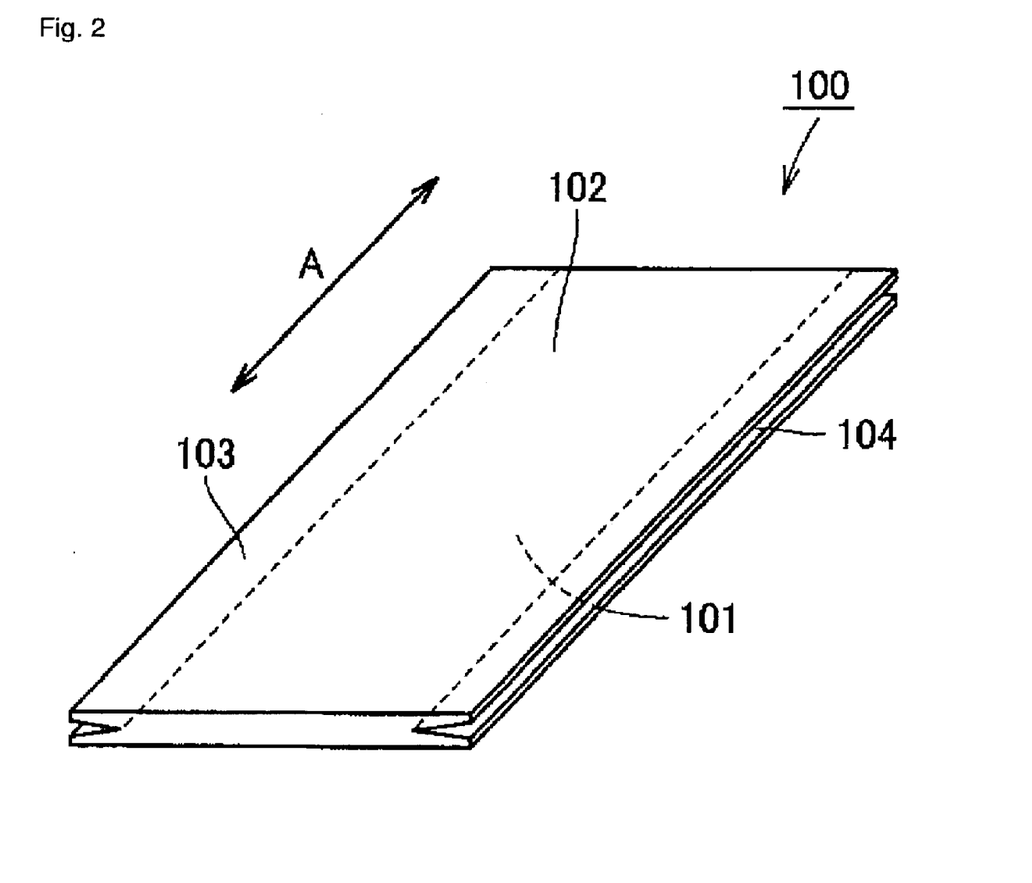
FIG. 2 is a perspective view showing the entire structure of the fluid bladder 100 for pressurizing according to the embodiment.

With reference to FIGS. 1 and 2, a structure of a fluid bladder 100 for pressurizing of this embodiment will be described. FIG. 1 is a cross sectional view showing the structure of the fluid bladder 100 for pressurizing, and FIG. 2 is a perspective view showing the entire structure of the fluid bladder 100 for pressurizing.

With reference to FIGS. 1 and 2, the fluid bladder 100 for pressurizing according to the embodiment of the invention has an inside belt 101, an outside belt 102, a first expandable portion 103 and a second expandable portion 104. The inside belt 101 is positioned on a side of the subject. The outside belt 102 is provided on a position opposed to the inside belt 101. The first expandable portion 103 and the second expandable portion 104 are provided so as to connect the inside belt 101 and the outside belt 102 on both the side portions with respect to a direction in which it is wound around a brachium, a wrist and the like (direction A in FIG. 2). When the fluid bladder 100 for pressurizing is deflated, as shown in FIG. 1, the first expandable portion 103 and the second expandable portion 104 are bent inward as shown in FIG. 1.

The first expandable portion 103 has a side portion 103a at an inside belt side whose one end is connected with the inside belt 101, and a side portion 103b at an outside belt side whose one end is connected with the outside belt 102. The other ends of the side portion 103a at the inside belt side and the side portion 103b at the outside belt side are connected, so that an approximately Σ shape is formed. The second expandable portion 104 also has a side portion 104a at the inside belt side and a side portion 104b at the outside belt side similarly to the first expandable portion 103.

In the embodiment, the inside belt 101, the outside belt 102, the first expandable portion 103 and the second expandable portion 104 are formed by the same material, such as vinyl chloride or urethane with a thickness of about 0.3 mm.

A width of the inside belt 101 and the outside belt 102 is set to a predetermined dimension W (for example, about 130 mm), and after the fluid bladder for pressurizing 100 is inflated, the width dimension W is approximately maintained.

As a characteristic structure in the embodiment, a distance d1 along the bending of the first expandable portion 103 is different from a length d2 along the bending of the second expandable portion 104 at the time of deflation. Specifically, the distance d2 along the bending of the second expandable portion 104 is longer than the distance d1 along the bending of the first expandable portion 103. For example, d1 is about 25 mm, and d2 is about 30 mm.

Figure 3:
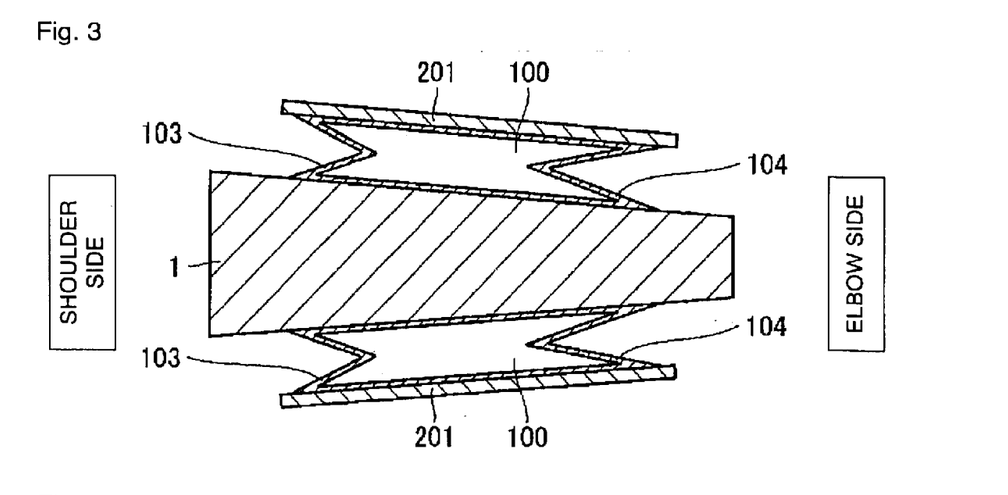
FIG. 3 is a schematic diagram showing a state where the fluid bladder 100 for pressurizing according to the embodiment is wound around a brachium 1 by a cuff fixing element 201 and the fluid bladder 100 for pressurizing is not inflated.
Figure 4:
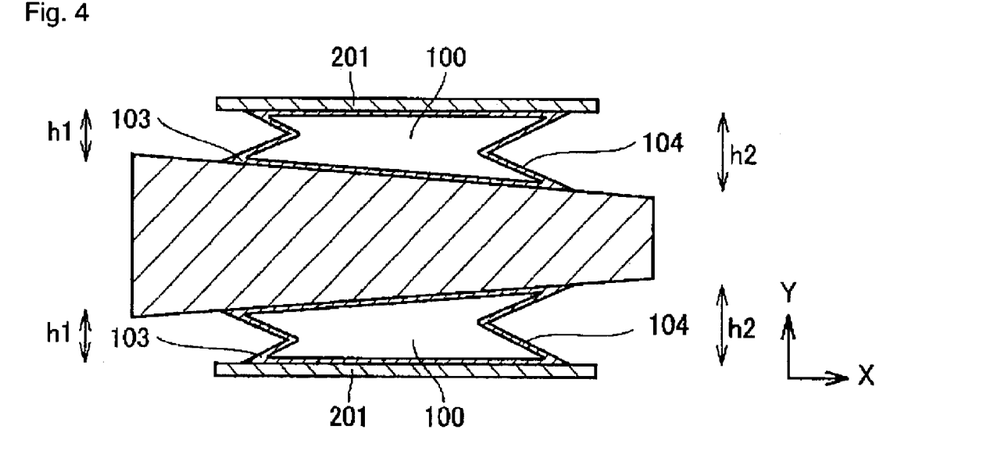
FIG. 4 is a schematic diagram showing a state where the fluid bladder 100 for pressurizing according to the embodiment is wound around the brachium 1 by the cuff fixing element 201 and the fluid bladder 100 for pressurizing is inflated.

Herein, FIG. 3 shows a state where the fluid bladder 100 for pressurizing is wound around the brachium 1 by the cuff fixing element 201 and the fluid bladder 100 for pressurizing is not inflated. FIG. 4 shows a state where the fluid bladder 100 for pressurizing is wound around the brachium 1 by the cuff fixing element 201 and the fluid bladder 100 for pressurizing is inflated.

As is clear from comparison of FIG. 3 with FIG. 4, the fluid bladder 100 for pressurizing can be inflated so that, after the fluid bladder 100 for pressurizing is inflated, the second expandable portion 104 expands longer than the first expandable portion 103 (h1<h2 in FIG. 4). As a result, it is confirmed that the cuff fixing element 201 is approximately parallel with the axial direction of the subject (X axial direction in FIG. 4).

Herein, with reference to FIGS. 5 to 8, the operational principle of the inflation of the fluid bladder 100 for pressurizing will be described in detail. FIGS. 5 to 8 are first to fourth schematic diagrams for describing the operational principle the inflation of the fluid bladder 100 for pressurizing.

Figure 5:
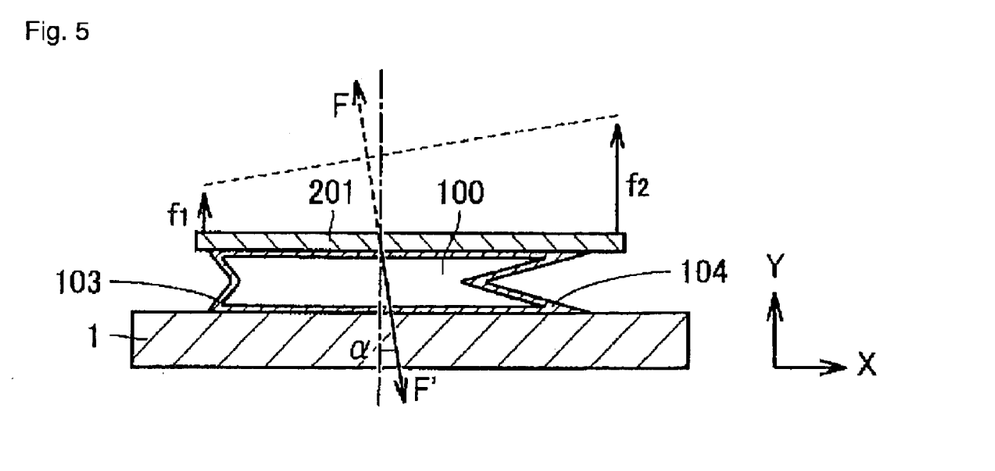
FIG. 5 is a first schematic diagram for describing operational principle of the inflation of the fluid bladder 100 for pressurizing according to the embodiment.
Figure 6:
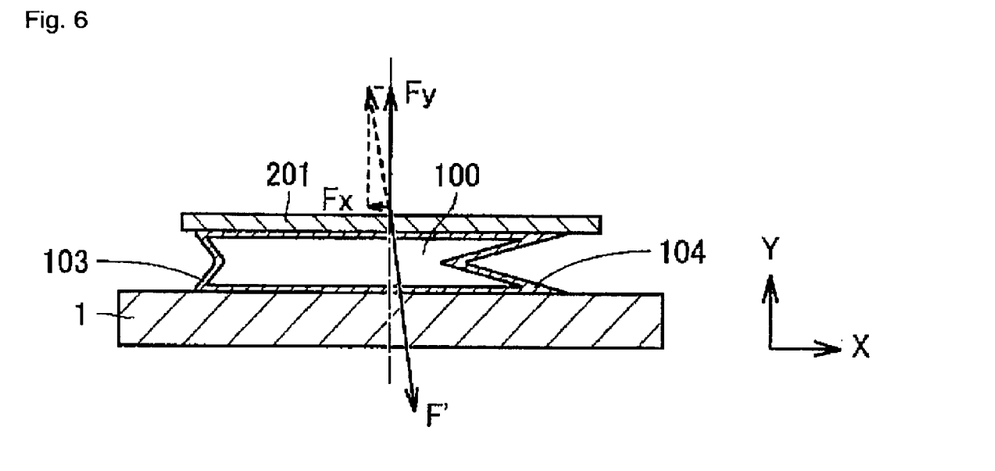
FIG. 6 is a second schematic diagram for describing the operational principle of the inflation of the fluid bladder 100 for pressurizing according to the embodiment.
Figure 7:
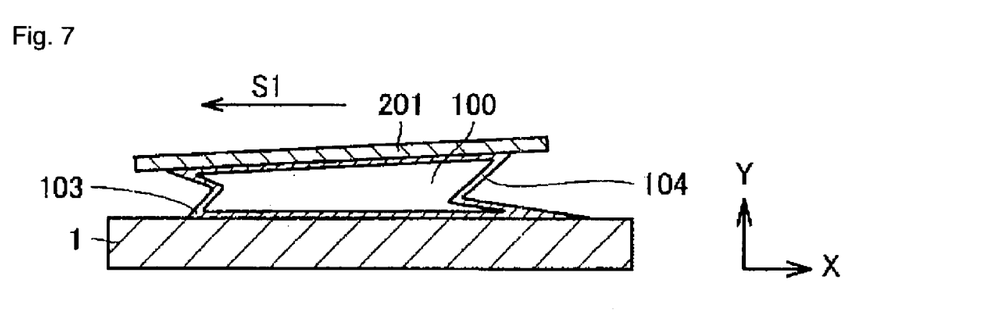
FIG. 7 is a third schematic diagram for describing the operational principle of the inflation of the fluid bladder 100 for pressurizing according to the embodiment.

With reference to FIG. 5, the case where the fluid bladder 100 for pressurizing is wound around the subject 1 in the horizontal state is considered. In the case where the fluid bladder 100 for pressurizing is inflated with a fluid fed thereinto, when the forces of the respective portions are represented by the forces f1, f2 acting on both the ends of the cuff fixing element 201, a relationship, f1<f2, is established because the second expandable portion 104 expands longer. For this reason, the force F, which is generated in the cuff fixing element 201 pushed by the fluid bladder 100 for pressurizing, is generated so as to face a direction tilted by α with respect to the axial direction of the subject (X axial direction in FIG. 5). When the balance of the forces is considered in this state, as shown in FIG. 6, force F-X which shifts to an -X axial direction is generated. When the force F-X is generated, therefore, the cuff fixing element 201 shifts to direction -X (direction S1 in FIG. 7) as shown in FIG. 7.

Figure 8:
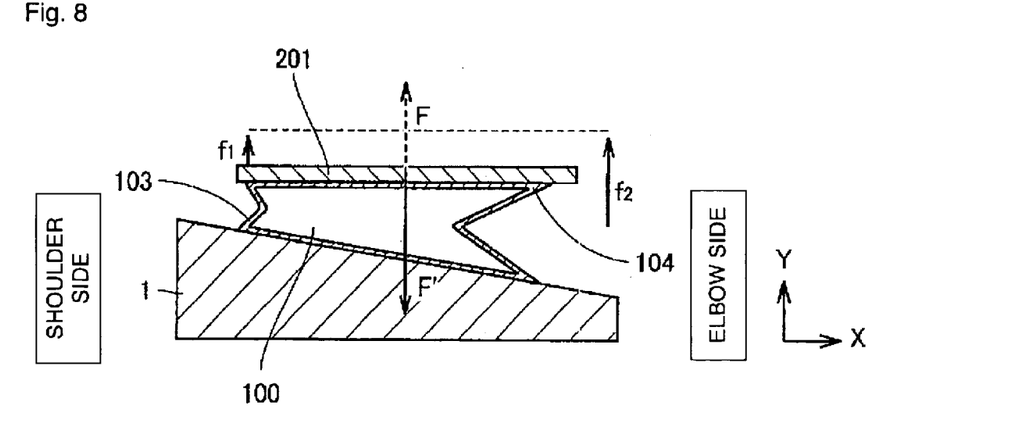
FIG. 8 is a fourth schematic diagram for describing the operational principle of the inflation of the fluid bladder 100 for pressurizing according to the embodiment.

The case where the fluid bladder 100 for pressurizing is wound around the subject 1 in the tapered state will be considered. In this case, as described referring to FIG. 18, the force FX which shifts to the X axial direction is generated on the cuff fixing element 201. In the fluid bladder 100 for pressurizing according to the embodiment, however, as described above, since the force F-X which shifts to the -X axial direction is generated, FX and F-X acts to opposite directions. As a result, the force which shifts to the X axial direction does not act on the cuff fixing element 201 in appearance. As a result, as shown in FIG. 8, the force F, which is generated on the cuff fixing element 201 when the cuff fixing element 201 is pushed by the fluid bladder for pressurizing 100, acts to the vertical direction (Y axial direction in FIG. 8) with respect to the axial direction of the subject (X axial direction in FIG. 8).

As a result, the tilt of the force generated on the cuff fixing element 201 pushed by the fluid bladder 100 for pressurizing is corrected, and thus the cuff fixing element 201 and the fluid bladder 100 for pressurizing do not shift to the elbow side, so that the pressure by the fluid bladder 100 for pressurizing is transmitted to the subject 1 efficiently. Excessive tension is not generated on the fluid bladder 100 for pressurizing, so that the fluid pump can be miniaturized and the pressure monitor can be miniaturized.

Figure 9:
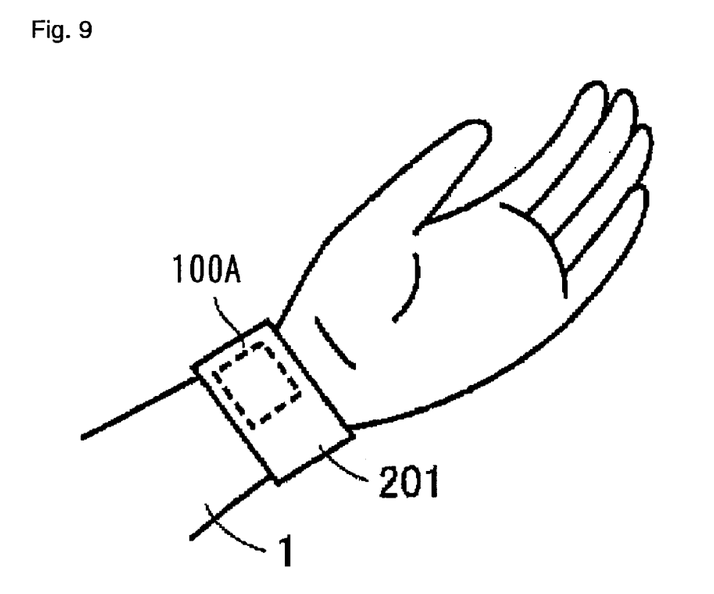
FIG. 9 is a diagram showing a state where a fluid bladder 100A for pressurizing according to another embodiment is mounted on a wrist.

The above embodiment describes the case where the cuff of the blood pressure monitor is wound around the brachium, but as shown in FIG. 9, the cuff can be applied to the fluid bladder 100A for pressurizing for locally pressurizing only a radius artery.

Figure 10:
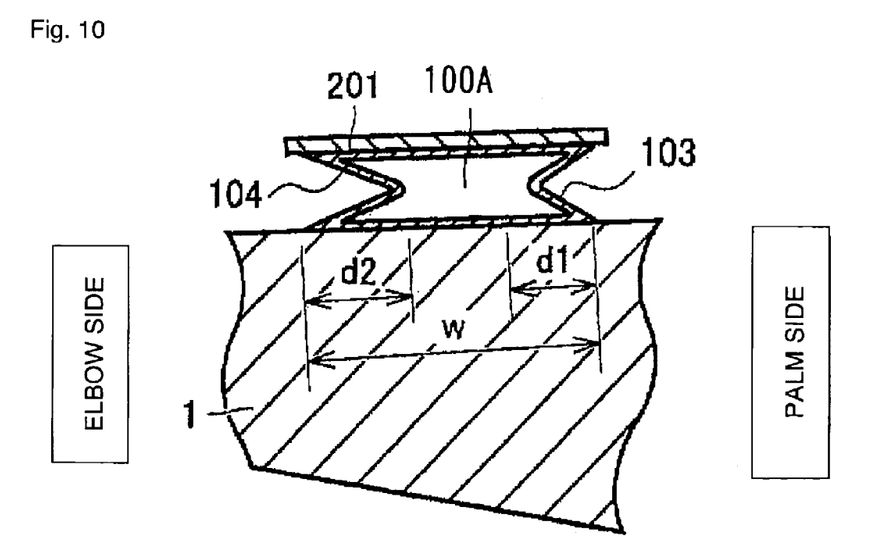
FIG. 10 is a diagram showing the fluid bladder 100A for pressurizing, according to the another embodiment, which locally pressurizes only radial artery on the wrist.

In the case of the fluid bladder 100A for pressurizing applied to the local pressurizing on the wrist, as shown in FIG. 10, since a portion on a palm side is thinner than a portion on an elbow side, the first expandable portion 103 is placed on the palm side and the second expandable portion 104 is placed on the elbow side, so that the effects similar to the above can be obtained.

In the above embodiment, the first expandable portion 103 and the second expandable portion 104 are the same member, and the distance along the bending of the first expandable portion 103 is set to be different from the distance along the bending of the second expandable portion 104, so that expandability of the first expandable portion 103 is different from expandability of the second expandable portion 104. In another structure of this embodiment, however, even when the distance along the bending of the first expandable portion 103 is the same as the distance along the bending of the second expandable portion 104, the expandability of the first expandable portion 103 may be set to be different from the expandability of the second expandable portion 104. For example, even when the same material is used for the first and second expandable portions 103, 104, their thickness may be set to be different from each other. Furthermore, different materials may be used for the first expandable portion 103 and the second expandable portion 104.

According to the cuff of the blood pressure monitor of the present invention, the cuff fixing element and the fluid bladder for pressurizing are prevented from shifting, so that the pressure by the fluid bladder for pressurizing can be transmitted to the subject (artery) efficiently. Since excessive tension is not generated in the fluid bladder for pressurizing, the fluid pump can be miniaturized and the pressure monitor can be miniaturized.

The above is a detailed description of a particular embodiment of the invention which is not intended to limit the invention to the embodiment described above. It is recognized that modifications within the scope of the invention will occur to persons skilled in the art. Such modifications and equivalents of the invention are included within the scope of this invention.

What is claimed is:

1. A cuff of a blood pressure monitor, the cuff being configured to be mounted on a predetermined portion of a subject and including a bladder configured to expand to pressurize the predetermined portion of the subject upon inflation with a fluid, the bladder comprising:

an inside belt configured to be placed over the predetermined portion of the subject when the cuff is mounted on the predetermined portion of the subject;

an outside belt disposed over the inside belt;

a first expandable portion connecting a longitudinal side of the inside belt and a corresponding side of the outside belt;

a second expandable portion connecting another longitudinal side of the inside belt and a corresponding side of the outside belt, the second expandable portion being configured to expand more than the first expandable portion when the bladder is inflated with the fluid for pressurizing the predetermined portion of the subject.

2. The cuff of a blood pressure monitor of claim 1, wherein the first and second expandable portions are configured to be bent inward when the bladder is not inflated with the fluid, and a distance along the bending of the second expandable portion between the inside and outside belts is longer than a distance along the bending of the first expandable portion between the inside and outside belts.

3. The cuff of a blood pressure monitor of claim 1, wherein the second expandable portion has a larger expansion per unit length upon the inflation with the fluid than the first expandable portion.

4. The cuff of a blood pressure monitor of claim 3, wherein the first and second expandable portions are made of a same material, and the second expandable portion is thinner than the first expandable portion.

5. The cuff of a blood pressure monitor of claim 3, wherein the second expandable portion is made of a material having a lower elastic coefficient than a material of which the first expandable portion is made.

* * * * *